US010753919B2

(12) United States Patent
Effler, Jr. et al.

(10) Patent No.: US 10,753,919 B2
(45) Date of Patent: Aug. 25, 2020

(54) METHODS AND SYSTEMS FOR MEASURING THE FORCES OF A SHRINK FILM

(71) Applicant: Dow Global Technologies LLC, Midland, MI (US)

(72) Inventors: Lawrence J. Effler, Jr., Rosharon, TX (US); Rashi Tiwari, Missouri City, TX (US); Matthew J. Turpin, Sanford, MI (US); Robert R. Cummer, Midland, MI (US); Lyndi R. Kennedy, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 334 days.

(21) Appl. No.: 15/553,712

(22) PCT Filed: Feb. 11, 2016

(86) PCT No.: PCT/US2016/017506
§ 371 (c)(1),
(2) Date: Aug. 25, 2017

(87) PCT Pub. No.: WO2016/137754
PCT Pub. Date: Sep. 1, 2016

(65) Prior Publication Data
US 2018/0238853 A1  Aug. 23, 2018

Related U.S. Application Data

(60) Provisional application No. 62/121,949, filed on Feb. 27, 2015.

(51) Int. Cl.
*G01N 25/72* (2006.01)
*G01N 33/44* (2006.01)

(52) U.S. Cl.
CPC .......... *G01N 33/442* (2013.01); *G01N 25/72* (2013.01); *G01N 2203/0003* (2013.01);
(Continued)

(58) Field of Classification Search
CPC ................. G01N 33/442; G01N 25/72; G01N 2203/0278; G01N 2203/0282;
(Continued)

(56) References Cited

U.S. PATENT DOCUMENTS 3,295,290 A * 1/1967 Billingsley ............. B65B 27/04
53/398
4,380,175 A   4/1983 Griffen
(Continued)

FOREIGN PATENT DOCUMENTS

EP   1268280   5/2004
EP   2653391   10/2013
(Continued)

OTHER PUBLICATIONS

Hong, "Thermal Behaviors of Heat Shrinkable Poly(vinyl chloride) Film", Journal of Applied Polymer Science, vol. 112, 886-895(2009), 2009 Wiley Periodicals, Inc.
(Continued)

*Primary Examiner* — Robert R Raevis
(74) *Attorney, Agent, or Firm* — Dinsmore & Shohl LLP

(57) ABSTRACT

According to one embodiment described herein, the forces of a shrink film may be measured. The method of measuring the forces may include providing a shrink film processing unit and a testing vehicle moveable within the shrink film processing unit, positioning a shrink film around the testing vehicle, processing the wrapped testing vehicle by shrinking the shrink film around the testing vehicle as the testing vehicle moves through the shrink film processing unit, and measuring the forces applied by the shrink film on the testing
(Continued)

vehicle with one or more force sensors at multiple separate sensor positions on the exterior of the testing vehicle during processing, after processing, or both.

19 Claims, 5 Drawing Sheets

(52) U.S. Cl.
CPC ........... *G01N 2203/0026* (2013.01); *G01N 2203/0067* (2013.01); *G01N 2203/0076* (2013.01); *G01N 2203/0278* (2013.01)

(58) Field of Classification Search
CPC ... G01N 2203/0003; G01N 2203/0026; G01N 2203/0067; G01N 2203/0076
USPC ....... 73/866, 862.043, 862.541, 159; 374/45, 374/55–57, 142; 264/40.1–40.7, 264/406–412; 53/556, 557, 441, 442
See application file for complete search history.

(56) References Cited

U.S. PATENT DOCUMENTS

| | | | |
|---|---|---|---|
| 6,340,532 B1 | 1/2002 | Huang et al. | |
| 6,742,380 B2 | 6/2004 | Johnston | |
| 6,785,072 B1 | 8/2004 | Willis et al. | |
| 8,859,671 B2 | 10/2014 | Tice et al. | |
| 2005/0201000 A1 | 9/2005 | Koh et al. | |
| 2008/0007271 A1 | 1/2008 | Smith et al. | |
| 2008/0303855 A1* | 12/2008 | Bidwell | B41J 2/17536 347/20 |
| 2011/0100139 A1* | 5/2011 | Parikh | G01L 5/008 73/862.041 |
| 2012/0130019 A1 | 5/2012 | Karjala et al. | |
| 2013/0146672 A1* | 6/2013 | DePaso | B65G 43/00 236/91 D |
| 2015/0076022 A1* | 3/2015 | Niedersuess | B65B 11/58 206/432 |

FOREIGN PATENT DOCUMENTS

| | | | |
|---|---|---|---|
| GB | 873220 | * | 7/1961 |
| RU | 002491214 | * | 8/2013 |
| WO | WO200062671 | | 10/2000 |
| WO | WO2013156533 | | 10/2013 |

OTHER PUBLICATIONS

International Search Report filed in International Application No. PCT/US2016/017506 dated May 30, 2016.
International Preliminary Report on Patentability filed in International Application No. PCT/US2016/017506 dated Sep. 8, 2017.
Bayley, "Critical Design Considerations for Polyethylene Materials in Collation Shrink Film", Nova Chemicals, 2008 Place Conference Sep. 14-17, 2008.
Wang-Shu, "Comparison of the Thermal Shrinkage Properties of Neat-shrinkable Films based on ISO Standard", Packaging Engineering, Feb. 28, 2015, pp. 54-58.
Office Action pertaining to corresponding Chinese Patent Application No. 20680009347.X, dated Aug. 6, 2019.
Communication pursuant to Article 94(3) EPC dated Jul. 9, 2018 pertaining to EP Patent App. No. 16708526.5, 4 Pages.
Highlight Industries, Inc. "Stretch Film Test Frame" dated Dec. 19, 2014.

* cited by examiner

METHODS AND SYSTEMS FOR MEASURING THE FORCES OF A SHRINK FILM

CROSS-REFERENCE TO RELATED APPLICATIONS

This application claims priority to U.S. Provisional Patent Application No. 62/121,949, filed Feb. 27, 2015, entitled "Methods And Systems For Measuring The Forces Of A Shrink Film", the contents of which are hereby incorporated by reference in their entirety.

TECHNICAL FIELD

The present disclosure generally relates to methods and systems for analyzing shrink films, and more specifically, to methods and systems for multi-positional measuring of the forces of a shrink film.

BACKGROUND

Shrink films are commonly used for packaging of products, such as consumer goods products. For example, bundles of plastic bottles or can be secured by a shrink film package that secures the plastic bottles together. Shrink films may include polymer films that are placed around an object and are shrunken relative to their original dimensions to at least partially surround the object and secure the item or items held within. For example, plastic beverage containers can be bundled and secured in shrink film. Advantages of shrink film over other traditional packaging, such as cardboard packaging, may include reduced environmental impact, cost savings, its ability to be see-through, and its ability to serve as both a packaging for shipping as well as for consumer display.

However, selecting appropriate shrink film materials and appropriate processing techniques can be difficult. For example, over-shrinking the shrink film may lead to a damaged product stored inside or breakage of the shrink film. On the other hand, under-shrinking the shrink film may lead to unsecured products which can fall out of the shrink film package. In short, the force needs to be strong enough to keep the bundled packages together as a unitized whole but not so strong as to damage the primary packages or the film itself. Accordingly, improved systems and methods for analyzing shrink films may be beneficial.

SUMMARY

Embodiments of the present disclosure are directed to systems and methods for observing the forces exerted by a shrink film which at last partially surrounds one or more objects (i.e., multiple objects may be bundled together by a shrink film). The forces can be observed during the shrinking process, and optionally, following shrinking. The observed force measurements can then be analyzed, and processing conditions for shrink film application may be altered based on the analyzed force measurements. Without being bound by theory, conventional analytical systems may not measure the forces at multiple locations on a shrink film, and as a result, these conventional systems may not measure the plurality of different forces exerted by the shrink film at various locations of the wrapped objects. For example, in conventional systems, forces may not be observed along the edges, near the top, near the bulls-eye, and/or at the corners of a shrink film package. On the other hand, the present embodiments utilize force sensors positioned at multiple positions which contact the shrink film to obtain a more accurate depiction of the forces across the entirety of the shrink film. Furthermore, without being bound by theory, conventional analytical systems may fail to appreciate the force fluctuations across the shrink film over the time period of the shrinking. The present embodiments may utilize force sensors positioned at multiple positions to measure force changes before, during and after the heating and cooling cycles of shrink film processing. For example, a force differential across the shrink film or a rapid force change at specific shrink film locations during shrinking may indicate shrink film integrity issues and, thus, the present embodiments provide actionable data which the skilled person may utilize to improve the shrink process to produce more robust shrink films.

In accordance with one embodiment of the present disclosure, a method for measuring the forces of a shrink film may comprise providing a shrink film processing unit and a testing vehicle. The testing vehicle may be moveable within the shrink film processing unit and may comprise a three-dimensional frame structure comprising length, width, and height dimensions. The testing vehicle may further comprise a plurality of force sensors positioned at multiple separate sensor positions proximate an outer surface of the three-dimensional frame structure. The plurality of force sensors may be arranged at multiple separate sensor positions in order to measure forces in the direction of the length, the width, and the height dimensions of the three-dimensional frame structure. The method for measuring the forces of the shrink film may also comprise positioning a shrink film around the testing vehicle, processing the wrapped testing vehicle by shrinking the shrink film around the testing vehicle as the testing vehicle moves through the shrink film processing unit, and measuring the forces applied by the shrink film on the testing vehicle with the force sensors at the multiple separate sensor positions during processing, after processing, or both. The testing vehicle may be at least partially wrapped by the shrink film in a non-shrunken state prior to the processing by shrinking.

In accordance with another embodiment of the present disclosure, a system may measure the force of shrink film. The system may comprise a shrink film processing unit and a testing vehicle moveable within the shrink film processing unit. The shrink film processing unit may comprise a heating zone and a cooling zone downstream of the heating zone. The testing vehicle may comprise a three-dimensional frame structure comprising length, width, and height dimensions. The testing vehicle may further comprise a plurality of force sensors positioned on multiple separate sensor positions proximate an outer surface of the three-dimensional frame structure. The plurality of force sensors may be arranged at multiple separate sensors positions in order to measure forces in the direction of the length, the width, and the height dimensions of the three-dimensional frame structure.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

It is to be understood that both the foregoing general description and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and together with the description serve to explain the principles and operations of the technology. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
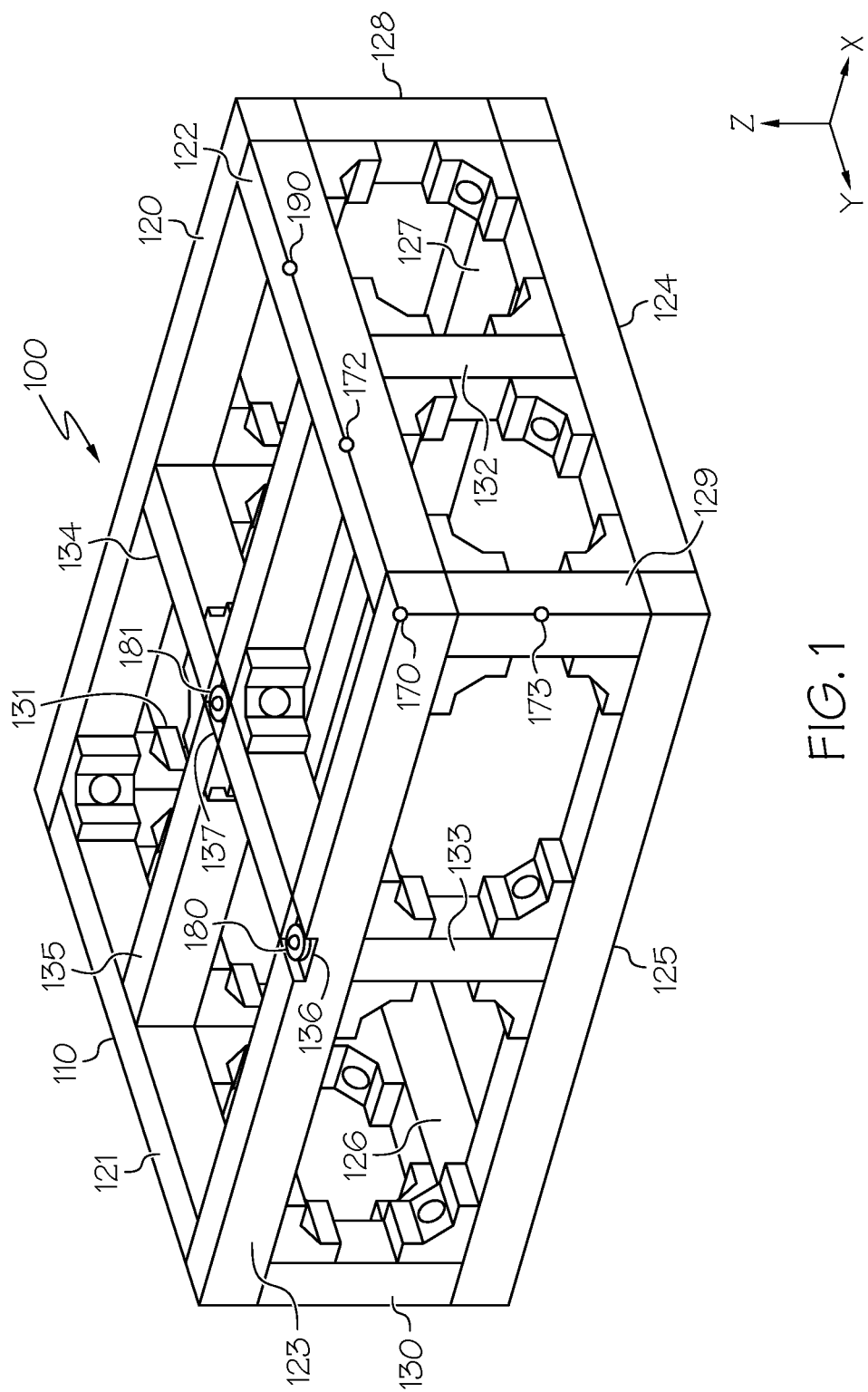
FIG. 1 is a perspective view of a testing vehicle prior to shrink wrap application, according to one or more embodiments described herein.

Reference will now be made in greater detail to various embodiments, some embodiments of which are illustrated in the accompanying drawings. Whenever possible, the same reference numerals will be used throughout the drawings to refer to the same or similar parts.

The embodiments disclosed herein are directed to systems and methods for measuring the forces of a shrink film. Generally, to apply a shrink film around an item or group of items, a shrink film material in a non-shrunken state is positioned around the objects and the shrink film is subsequently shrunken. The shrinking process may involve heating and cooling by conventional or other means. As the shrink film is shrunken around the one or more items, it exerts a force on the items. The methods and systems described herein generally measure the forces exerted by the shrink film on the wrapped item. The methods and systems may measure the forces at various locations of the item and throughout the shrinking process. For example, the methods and systems described herein may measure the forces exerted by the shrink film during shrinking and following shrinking. In one embodiment, the forces may be measured by a testing vehicle, where the testing vehicle includes sensors on multiple separate sensor positions proximate the outer surface of the testing vehicle. The plurality of sensors can measure the forces exerted by the shrink film on the outer surface of the testing vehicle prior to the shrink film being shrunken, as the shrink film is shrunken, and following shrinking.

As used herein, the term "shrink film" refers to any polymer film material that can be shrunken to fit around and secure one or more items. Without being bound by theory, shrinkage in shrink films may occur due to relaxation of the orientation stresses of the plastics during the shrink process. Shrink films may include polymers such as, but not limited to, polyolefins such as polypropylene and polyethylene. Polyethylene films may include one or more of low density polyethylene (LDPE), linear low density polyethylene (LLDPE), medium density polyethylene, or high density polyethylene (HDPE)). Other plastics such as polyvinyl chloride are also contemplated. Shrink films may be in multi-layer structures, or in a monolayer structure. In exemplary embodiments, monolayer structures, which are often used in logistics and distribution markets (e.g., pallet wrapping) may include predominately LDPE with some LLDPE for tear and puncture resistance and HDPE for stiffness. As these films are intended to be removed from the bundle prior to stocking the retail store shelf, the haziness imparted by the HDPE is not a concern. In contrast, multilayer layer structures, which may be used in retail products, may include high clarity skin layers that are mostly LLDPE with some LDPE and a core layer that is largely LDPE with some LLDPE. In one embodiment, the LLDPE/LDPE ratio by weight in the skin layer is about 80/20 while the core is about a 30/70 ratio. In additional embodiments, the LLDPE/LDPE ratio by weight in the skin layer may be about 95/5, about 90/10, about 85/15, about 75/25, about 70/30, about 65/35, or in a range from about 75/25 to about 85/15, or about 70/30 to about 90/10; and the LLDPE/LDPE ratio by weight in the core may be about 50/50, about 45/55, about 40/60, about 35/65, about 25/75, about 20/80, about 15/85, or in a rage from about 25/75 to about 35/65, or from about 20/80 to about 40/60.

Moreover, shrink films may be substantially transparent or "see-through" or alternatively may be opaque. Shrink films may be opaque based on the composition of the shrink film or, in other embodiments, a transparent shrink film may be colored by a printing or a similar process (i.e., to mark a product with a brand image or trademark). It should be understood that some embodiments of shrink films are commonly referred to as "collation shrink films" and that such are contemplated herein.

Additionally, as used herein, "measuring forces" should be understood to refer to measuring forces exerted by the shrink wrap and is inclusive or any other unit that reflects force, such as, but not limited to, pressure (i.e., force per unit area). For example, measuring forces should be understood as inclusive of collecting data in terms of force (i.e., in Newtons) or in terms of pressure (i.e, in Pascals). In embodiments therein, sensors on the testing vehicle may collect data in terms of force or pressure.

Without being bound by theory, the magnitude of the force exerted may be caused by several factors. First, the force may be impacted by the resin compositions and layer structures that comprise the film, specifically the properties and parameters related to the composition and structure. These parameters may include, but are not limited to, the ratio of LDPE to LLDPE, autoclave versus tubular LDPE compositions, molecular weights and molecular weight distributions of the film, balanced versus unbalanced layer structures, film thicknesses, etc. Second, the film fabrication conditions may impact the forces, for example, the melt temperatures, blow up ratios, draw down and cooling conditions, production rate, die gap, and/or frost line height. Third, the force may be impacted by the shrink processing unit (e.g., shrink tunnel) conditions, for example, tunnel temperatures and profiles, air speed, air flow conditions, residence time, etc. Differences in any of these conditions can affect the final performance of the film itself. Thus, having a means to measure and monitor the forces exerted by the shrink film during the shrinking process can be useful in understanding how to design, process and use shrink films in the most effective manner.

Referring now to FIG. 1, one embodiment of a testing vehicle 100 is depicted. The testing vehicle 100 may comprise a three-dimensional frame structure 110 comprising length, width, and height dimensions. As shown in FIG. 1, the length, width, and height dimensions of the testing vehicle 100 may correspond with the x-axis, y-axis, and z-axis depicted in FIG. 1, respectively. The frame structure 110 may generally comprise a plurality of beams or other mechanical features which intersect or connect to form a three dimensional shape. For example, frames may intersect at locations other than their ends, or may be connected in any manner. For example, in the embodiment depicted in FIG. 1, three-dimensional frame structure 110 comprises a generally rectangular prism shape. However, it should be understood that the frame structure 110 may be any shape, such as, for example, any shape substantially matching that of a product or plurality of bundled products that may be housed in a shrink film 150. For example, the frame structure 110 may mimic the shape of a bundled commercial product. In embodiments, the frame structure 110, which may include any three-dimensional shape, may form, without limitation, a substantially triangular prism shape, a substantially hexagonal prism shape, a substantially pentagonal prism shape, a substantially conical shape, a substantially pyramidal shape, or a substantially cylindrical shape. While the testing vehicle 100 may move through a shrink film processing unit, it need not be capable of moving on its own.

As shown in the embodiment of FIG. 1, the frame structure 110 may comprise a plurality of horizontal beams and vertical beams which define the shape of the testing vehicle 100. The bottom beams 124, 125, 126, 127 may at least in part form a bottom surface of the frame structure 110 and the top beams 120, 121, 122, 123 may at least in part form a top surface of the frame structure 110. Additionally, side beams 128, 129, 130, 131 may connect the bottom beams 124, 125, 126, 127 with the top beams 120, 121, 122, 123 to form a rectangular prism. Other beam members, for example, beams 132, 133, 134, 135 may further interconnect the beams of the frame structure 110. Generally, the surface formed by the intersection of the top beams 120, 121, 122, 123 may be referred to herein as the top surface of the frame structure 110, the surface formed by the intersection of the bottom beams 124, 125, 126, 127 may be referred to herein as the bottom surface of the frame structure 110, and surfaces formed by the intersection of the side beams 128, 129, 130, 131 with the top beams 120, 121, 122, 123 and bottom beams 124, 125, 126, 127 may be referred to herein as the side surfaces.

In some embodiments, the three-dimensional frame structure 110 may be size-adjustable, where the frame structure 110 may change sizes. For example, one or more of the beams may be extendable and/or retractable, such as by telescoping or any other like mechanism. In other embodiments, the three-dimensional frame structure 110 may be disassemblable such that additional frame elements (i.e., additional beams) may be added to the frame structure to change the size of the frame structure.

In embodiments, the testing vehicle 100 may comprise one or more sensors. The term "sensor," as used herein, means a device that measures a physical quantity and converts it into a data signal, which is correlated to the measured value of the physical quantity, such as, for example, an electrical signal, an electromagnetic signal, an optical signal, a mechanical signal, or the like. Examples of sensors may include, without limitation: force sensors, which measure the force or pressure exerted upon the sensor; thermocouples, which are operable to determine the temperature of the surrounding environment; audio sensors; or cameras.

In one embodiment, the testing vehicle 100 comprises a plurality of force sensors 170, 172, 173, 180, 181. The force sensors 170, 172, 173, 180, 181 may comprise load cells. Generally, a load cell may be any transducer that is used to create an electrical signal whose magnitude is directly proportional to the force being measured. Various types of load cells, without limitation, include hydraulic load cells, pneumatic load cells and strain gauge load cells. The force sensors 170, 172, 173, 180, 181 may have varying measurement ranges. For example, force sensor 180, which is disposed on the perimeter of the testing vehicle 100, may more precisely measure lower forces, such as a maximum force of 20 g, while force sensor 181, which is centrally located on the top surface of the testing vehicle 100, may be operable to measure relatively higher maximum forces, such as 50 lbf, or even higher. Commercially available load cells suitable for the present embodiments may be the LSB200 Miniature S-Beam Load Cell and/or the LLB300 Subminiature Load Button produced by Futek.

Figure 2:
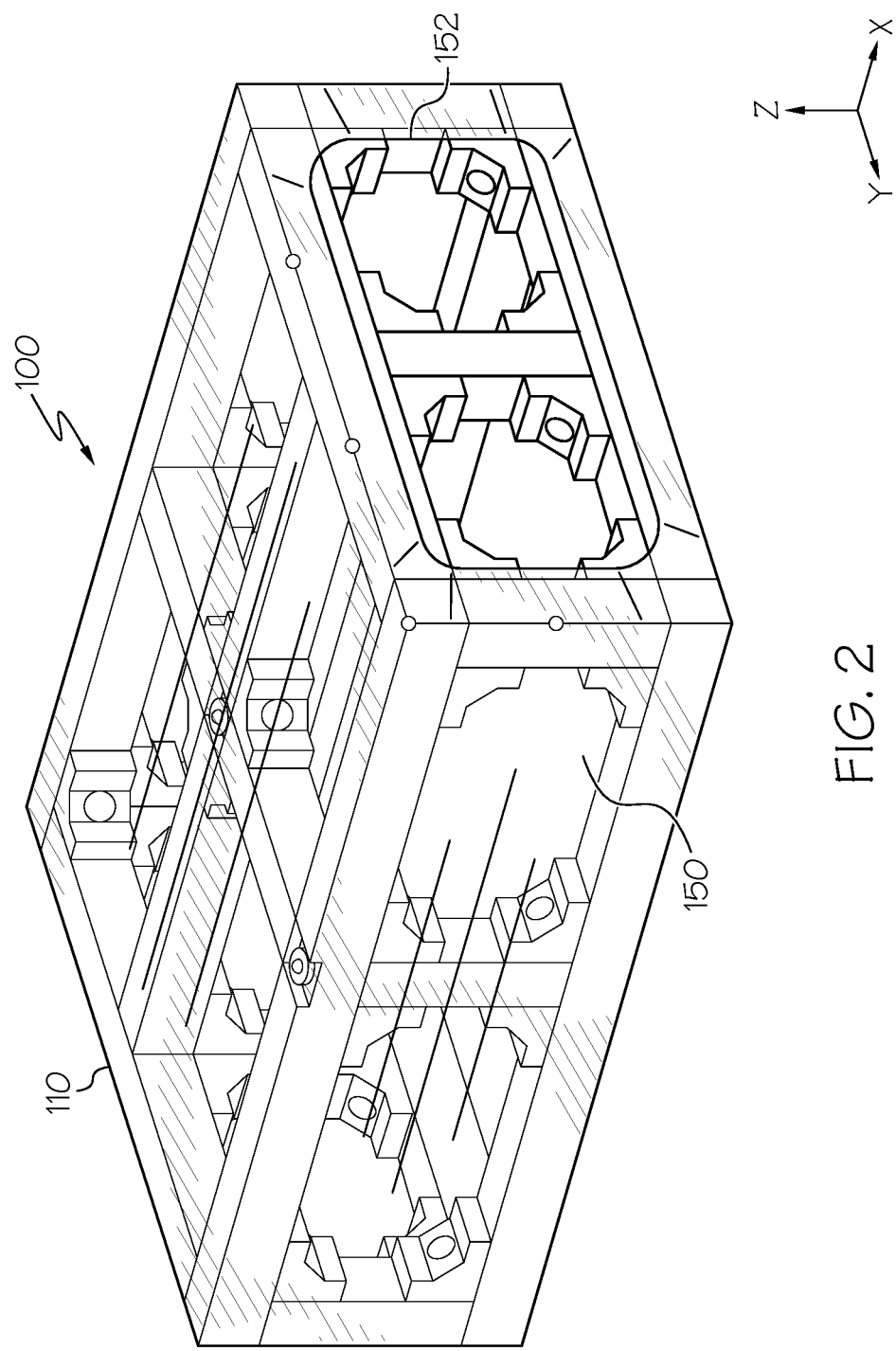
FIG. 2 is another perspective view of the testing vehicle of FIG. 1 surrounded by shrink film, according to one or more embodiments described herein.

The force sensors 170, 172, 173, 180, 181 may be positioned at multiple separate sensor positions. Each of the sensor positions are proximate an outer surface of the three-dimensional frame structure 110, as shown in FIG. 1. The term "outer surface" generally refers to any surface of the three-dimensional frame structure 110 which faces outwardly relative to its bulk three dimensional shape. Furthermore, a sensor's positioning refers to the positioning of the portion of the sensor that is exposed to the measured physical phenomena. For example, FIG. 2 shows the testing vehicle 100 of FIG. 1 surrounded in shrink film 150 (where edge 152 of shrink film 150 is shown). Any area of the frame structure 110 which is contacted by shrink film 150 is considered the outer surface. Edge 152 of the shrink film 150 may generally shrink around a side of the testing vehicle 100 to form a "bull's-eye" opening in the shrink film 150. The portions of the force sensors which make contact with the shrink film 150 are proximate the outer surface of the frame structure 110.

In one or more embodiments, the force sensors 170, 172, 173, 180, 181 may be appropriately arranged to measure forces in the direction of the length, the width, and the height dimensions of the three-dimensional frame structure 110. In embodiments, the force sensors 170, 172, 173, 180, 181 may be positioned on outer faces, outer corners, and/or outer edges of the outer surface of the three-dimensional frame structure 110. Referring to FIG. 1, force sensors 180 and 181 are positioned on the top outer face of the frame structure 110, force sensor 170 is positioned on an outer corner of the frame structure 110, and force sensors 172 and 173 are positioned on outer edges of the frame structure 110. While FIG. 1 depicts five force sensors, it should be understood that any number of force sensors may be employed, such as, without limitation, 1, 2, 3, 4, 5, 6, 7, 8, 9, 10, 11, 12, 13, 14, 15, or even more force sensors on a single testing vehicle 100.

Figure 3:
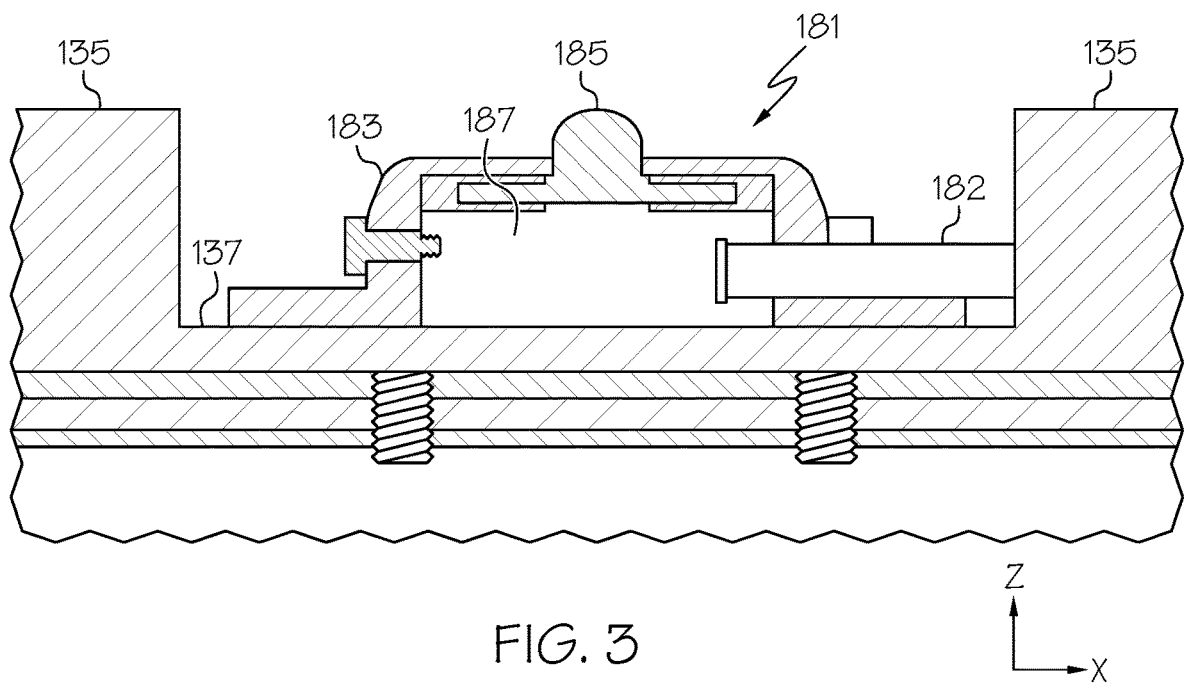
FIG. 3 is a cross-sectional view of a top force sensor on the testing vehicle of FIG. 1, according to one or more embodiments described herein.

Referring now to FIGS. 1 and 3, force sensor 181 is positioned on an outer face within a depression 137 in the beam 135. As shown in FIG. 3, in one embodiment, the force sensor 181 positioned on an outer face may comprise a button plate sensor configuration. In such a configuration, the force sensor 181 may comprise an actuator body 185 which may be partially encased by a button housing 183. The actuator body 185 may be pressed down by an external force (i.e., from a shrink film) into a measurement cell 187 and the movement of the actuator body 185 may be converted to force data by the measurement cell 187. The top of the actuator body 185 may be slightly raised from the non-depressed height of the beam 135. As such, when the shrink film 150 contacts the frame structure 110 it will press down on the force sensor 181 with an applied force. In embodiments, the force sensor 181 may be held in position by a mechanical fastening device 182, but may alternatively be held in position by an adhesive or by any other suitable mechanical fastening means.

While only two outer-face force sensors 180, 181 are shown in the embodiment of FIG. 1, the testing vehicle 100 may comprise any number of force sensors 180, 181 that are positioned on the outer face of the frame structure 110. In such embodiments, the frame structure 110 may comprise a depression 136, 137 for each force sensor 180, 181 which is positioned on an outer face.

Figure 4:
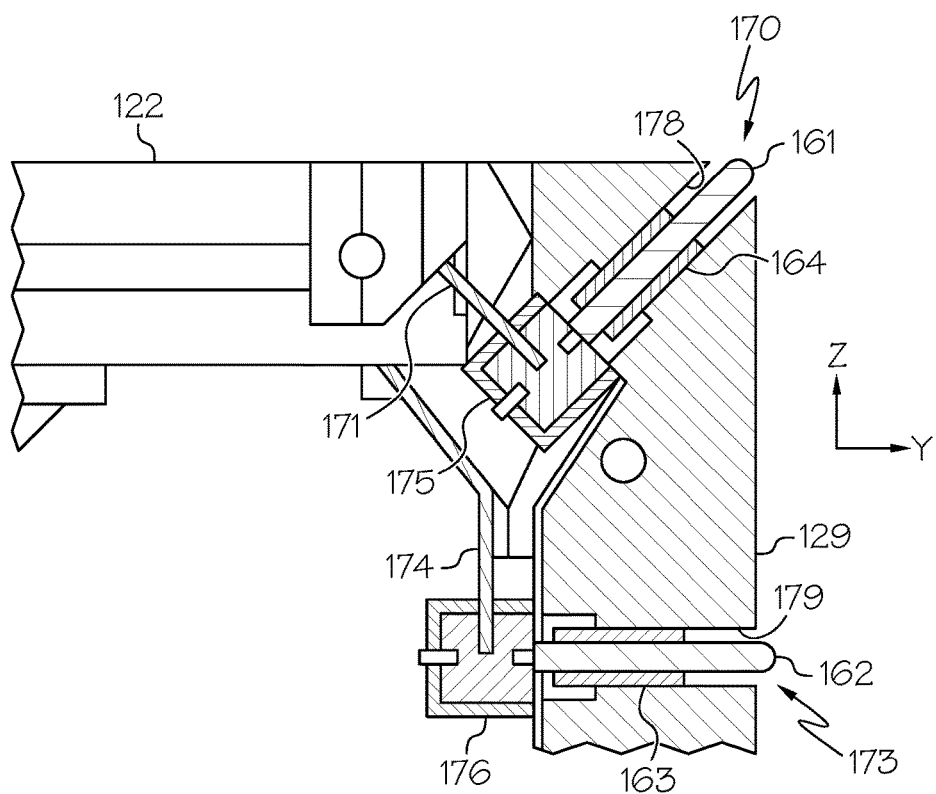
FIG. 4 is a cross-sectional view of a corner and edge force sensor on the testing vehicle of FIG. 1, according to one or more embodiments described herein.

Now referring to FIGS. 1 and 4, force sensors 170 and 173 are depicted in a cross sectional view of the frame structure 110. Force sensor 170 is positioned proximate an outer corner of the frame structure and force sensor 173 is positioned proximate an outer edge of the frame structure 110. As shown in FIG. 4, in one embodiment, force sensors 170, 173 may comprise a sliding pin sensor configuration. In such a configuration, the force sensors 170, 173 may each comprise a pin member 161, 162 which fits into a channel 178, 179 in the frame structure 110. The pin member 161, 162 may be pushed down by an external force (i.e., from a shrink film 150) into a measurement cell 175, 176 and the movement of the pin member 161, 162 may be converted to force data by the measurement cell 175, 176. In embodiments, the force sensors 170, 173 may be held in position by mechanical fastening devices 171, 174 but may alternatively be held in position by an adhesive or by any other suitable mechanical fastening means. A bushing 163, 164 may be positioned within the channel 178, 179 which secures the slidable positioning of the pin member 161, 162 within the channel 178, 179.

The force sensor 170 positioned proximate the outer corner of the frame structure 110 may generally have its pin member 161 facing outwardly and away from the corner, such as at approximately a 45° angle relative to the x-axis, y-axis, and z-axis. The force sensor 173 positioned proximate an outer edge of the frame structure 110 may generally have its pin member 162 facing outwardly and away from the outer edge, such as at approximately a 45° angle relative to the x-axis, y-axis, and at approximately a 90° angle relative to the z-axis. However, it should be understood that the force sensors located on the frame structure 110 may generally point in any direction and measure forces applied on the frame structure in any direction.

In one embodiment, the testing vehicle 100 may comprise one or more temperature-measuring devices 190. A temperature-measuring device 190 may generally be any device operable to measure temperature, and may be placed on or near the outer surface of the frame structure 110. The temperature-measuring device 190 may be in contact or at least near the shrink film 150 while the shrink film 150 is shrunken during processing. In embodiments, the temperature-measuring device may comprise a thermometer, a thermocouple, or any other suitable device.

It should be understood that while the embodiments depicted in the drawings have a particular number of sensors identified, embodiments of the testing vehicle 100 described herein may have any number of sensors and those sensors may be positioned at any outer edge, outer corner, outer face, or other outer physical feature of the testing vehicle 100.

Figure 5:
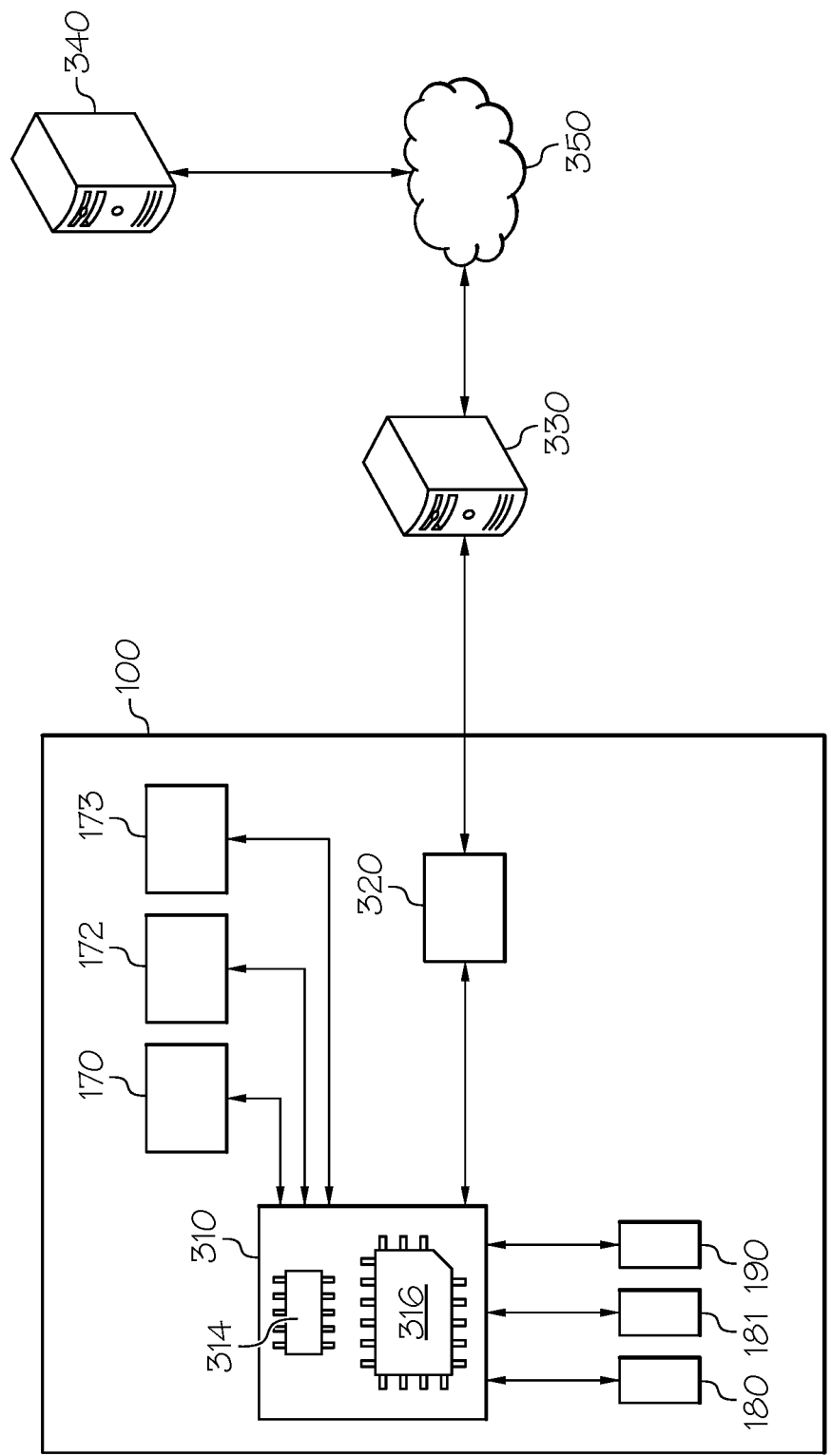
FIG. 5 schematically depicts a network system communicatively coupled to the testing vehicle of FIG. 1, according to one or more embodiments described herein.

In one embodiment, the testing vehicle 100 may further comprise a controller 310 (not shown in FIG. 1) comprising a processor 316 and memory 314, which is communicatively coupled with the force sensors or other sensors through one or more communication paths (shown in FIG. 5 as double sided arrows). The controller 310 can be coupled to any interior portion of the testing vehicle 100. Alternatively, the controller 310 may be located external of the testing vehicle 100 where, for example, the sensors may be connected by wires to a detached controller 310. According to the embodiments described herein, a processor 316 means any device capable of executing machine readable instructions. Accordingly, the processor 316 may be an integrated circuit, a microchip, a computer, or any other computing device. The memory 314 described herein may be RAM, ROM, a flash memory, a hard drive, or any device capable of storing machine readable instructions. Embodiments of the present disclosure comprise logic that includes machine readable instructions or an algorithm written in any programming language of any generation (e.g., 1 GL, 2 GL, 3 GL, 4 GL, or 5 GL) such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the logic or algorithm may be written in a hardware description language (HDL), such as logic implemented via either a field-programmable gate array (FPGA) configuration or an application-specific integrated circuit (ASIC), and their equivalents. Accordingly, the logic may be implemented in any conventional computer programming language, as pre-programmed hardware elements, or as a combination of hardware and software components.

The communication paths may provide data interconnectivity between various modules disposed on the testing vehicle 100. As used herein, a module may be any device communicatively coupled with the controller 310. Accordingly, a communication path 312 may communicatively couple any number of modules with one another, and may allow the modules to operate in a distributed computing environment. Specifically, each of the modules can operate as a node that may send and/or receive data. In one embodiment, the communication paths may can comprise a conductive material that permits the transmission of electrical data signals to processors, memories, sensors, and actuators throughout the testing vehicle 100. In one embodiment, the communication paths may comprise one or more conductive wires which allow for data transmission between modules. In another embodiment, the communication path 104 can be a bus, such as for example a LIN bus, a CAN bus, a VAN bus, and the like. In further embodiments, the communication path 312 may be wireless or, alternatively, an optical waveguide. As used herein, the term "communicatively coupled" means that the components are capable of exchanging data signals with one another such as, for example, electrical signals via conductive medium, electromagnetic signals via air, optical signals via optical waveguides, and the like. In one embodiment, modules may be communicatively coupled when removable storage devices are interchanged between the modules, such as a memory stick, memory card, or other writable medium. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. Additionally, it should be understood that the testing vehicle 100 may include a plurality of modules each having one or more processors that are communicatively coupled with one or more of the other components. Thus, the embodiments described herein may utilize a distributed computing arrangement to perform any portion of the logic described herein.

The controller 310 may be communicatively coupled to one or more of the sensors, such as the force sensors 170, 172, 173, 180, 181 or the temperature-measuring device 190. The controller 310 may receive force data from the force sensors 170, 172, 173, 180, 181 located on the testing vehicle 100 to store the forces exerted on the testing vehicle 100 by the shrink film 150. Such force data may be utilized to analyze shrink films and shrinking processes where varying materials, bundled items, and/or processing conditions are present. For example, shrink film forces on the testing vehicle 100 can be affected by the composition of the shrink film and/or the processing conditions of the shrinking (i.e., thermal treatment regimes).

As depicted in FIG. 5, the testing vehicle 100 may be in communication with an external computer 330. The external computer 330 can comprise one or more processors and one or more memories. The external computer 330 may be any personal computer such as a PC, laptop, tablet computer, server, or the like. The external computer 330 may be communicatively coupled with the testing vehicle 100.

In one embodiment, the vehicle 102 comprises data transmission device 320 for communicatively coupling the testing vehicle 100 with an external computer 330. The data transmission device 320 can be communicatively coupled to the controller 310 and can be any device capable of transmitting to and/or receiving data to and/or from the external computer 330. Accordingly, the data transmission device 320 can include an antenna and/or other communication transceiver for sending and/or receiving any wired or wireless communication. For example, the data transmission device 320 may include an antenna, a modem, LAN port, wireless fidelity (Wi-Fi) card, WiMax card, mobile communications hardware, near-field communication hardware, satellite communication hardware, global positing system interaction hardware, and/or any wired or wireless hardware for communicating with the external computer 330. In other embodiments, communication between the testing vehicle 100 and the external computer 330 may be facilitated by a hard memory device, such as a recordable disk or memory stick that is moved between the testing vehicle 100 and the external computer 330.

In one embodiment, the force data may be transferred from the controller 310 to the external computer 330. The force data may be displayed by the external computer 330 and may be analyzed by analytical tools, such as programs or software, available on the external computer 330. In one embodiment, the external computer 330 may be communicatively connected to a network 350 that may include one or more cellular networks, satellite networks and/or computer networks such as, for example, a wide area network, a local area network, personal area network, a global positioning system and combinations thereof. The network 350 may comprise access to the world wide web and may communicatively connect the testing vehicle 100 and/or the external computer 330 a remote computing device 340. Accordingly, the external computer 330 can be communicatively coupled to the network 350 via wires, via a wide area network, via a local area network, via a personal area network, via a cellular network, via a satellite network and the like. Suitable local area networks may include wired ethernet and/or wireless technologies such as, for example, Wi-Fi. Suitable personal area networks may include wireless technologies such as, for example, IrDA, Bluetooth, Wireless USB, Z-Wave, ZigBee, and the like. Alternatively or additionally, suitable personal area networks may include wired computer buses such as, for example, USB and FireWire. Suitable cellular networks include, but are not limited to, technologies such as LTE, WiMAX, UMTS, CDMA, and GSM.

As is noted above, the testing vehicle 100 can be communicatively coupled to the one or more remote computing devices 340 via the network 350. The one or more remote computing devices 340 may comprise one or more processors and one or more memories. The one or more processors can execute logic to provide cloud resources to the external computer 330 to analyze the force data. For example, the one or more remote computing devices 340 can provide supplementary processing power, via relatively high powered processors, to the external computer 330 to analyze the force data. Additionally, the one or more remote computing devices 340 can provide supplementary data storage to the controller 310 and/or external computer 330. Moreover, the remote computing device 240 can provide database information that may be suitable for analyzing force data.

For example, in one embodiment, force data collected by the testing vehicle may be displayed for viewing on the external computer 330 which is physically located at or near a manufacturing facility where the testing vehicle 100 is located. The external computer 330 may relay the force data to the remote computing device 340, which may be a remotely located server, and the remote computing device 340 may analyze the force data and send recommendations for shrink film processing alternations to the external computer 330.

In one embodiment, the sensors may be communicatively coupled to an AT32U4 microcontroller available from Atmel. The microcontroller may be coupled with a Linux processor which can either write the force data to a removable memory card, such as an SD card, or may transfer the force data to a desktop computer through a WiFi network. The desktop computer may store the force data, display the data, and/or analyze the data in any way.

Figure 6:
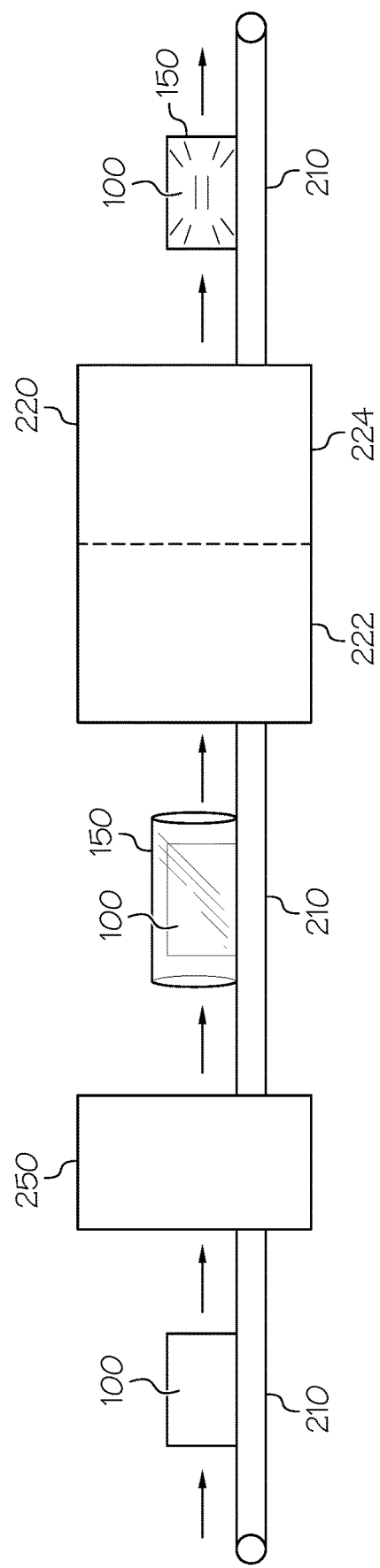
FIG. 6 schematically depicts a system comprising the shrink film processing unit, and the testing vehicle moveable therethrough, according to one or more embodiments described herein.

The method for measuring the forces of a shrink film 150 may generally comprise providing a testing vehicle 100, as described above, providing a shrink film processing unit 200, and monitoring the forces of a shrink film 150 as it is processed to shrink around the testing vehicle 100. Referring now to FIG. 6, one embodiment of a shrink film processing unit 200 is depicted. In one embodiment, the shrink film processing unit 200 may comprise a conveyor 210 and a shrink tunnel 220. Generally, the testing vehicle 100 may be at least partially wrapped with a shrink film 150 in a non-shrunken state and may be conveyed by the conveyor 210 through the shrink tunnel 220. As the testing vehicle 100 then moves through the shrink tunnel 220, the shrink film 150 undergoes shrinking which contracts the shrink film 150 around the testing vehicle 100. The shrink film 150 may be manually positioned around the testing vehicle 100 or may be positioned around the testing vehicle 100 by film applicator 250, as shown in FIG. 6. A film applicator 250, which may be positioned upstream of the shrink tunnel 220, may be automated to apply a shrink film 150 (in a non-shrunken state) around the testing vehicle 100 prior to the shrinking of the shrink film 150.

The shrink tunnel 220 may comprise a heating zone 222 and a cooling zone 224 downstream of the heating zone. As used herein, "downstream" refers to the direction of the conveyor 210, which is depicted by arrows in FIG. 6. The shrink film 150 is heated in the heating zone 222 and is subsequently cooled in the cooling zone 224. In one embodiment, the shrink film 150 is heated to a temperature of at least about 110° C. Following heating, the shrink film 150 may be cooled to a temperature at or below about 50° C. For example, the shrink film 150 may enter the shrink tunnel 220 at ambient temperature. As used herein "ambient temperature" refers to the temperature of the surrounding manufacturing environment, i.e. about room temperature, which may be from about 20° C. to about 26° C. It should be understood that while the cooling zone 224 is depicted in FIG. 6 as a portion of a shrink tunnel 220, the cooling zone 224 may be outside of the architecture of a shrink tunnel 220, for example, where the shrink tunnel 220 comprises a heating zone 222 which heats the shrink film 150 and the testing vehicle 100 then exits the shrink tunnel 220 and cools by blown air or cooling by exposure to ambient conditions in a cooling zone 224.

The shrink film 150 may be heated to at least about 90° C., at least about 100° C., at least about 110° C., at least about 120° C., at least about 130° C., at least about 140° C., at least about 120° C., at least about 125° C., 130° C., at least about 135° C., at least about 140° C., at least about 150° C., at least about 160° C., at least about 170° C., at least about 180° C., at least about 190° C., at least about 200° C., at least about 210° C., at least about 220° C., at least about 230° C., at least about 240° C., or even greater than 250° C. In embodiments, the shrink film 150 may be heated to a temperature in the range of from about 90° C. to about 250° C., from about 120° C. to about 250° C., from about 150° C. to about 250° C., from about 180° C. to about 150° C., from about 200° C. to about 250° C., from about 90° C. to about 230° C., from about 90° C. to about 200° C., from about 90° C. to about 170° C., from about 90° C. to about 150° C., from about 170° C. to about 220° C., or from about 160° C. to about 230° C. The heating hold time may be from about 1 second to about several minutes, from about 2 seconds to about 1 minute, from about 3 seconds to about 30 seconds, from about 5 seconds to about 20 seconds, or from about 10 seconds to about 15 seconds.

Following heating, the shrink film 150 may be cooled in the cooling zone 224. The cooling may be a passive cooling, where the cooling is naturally brought about by exposure to ambient temperatures in substantially still air, or the cooling may be active cooling. For active cooling, in embodiments, a stream of air may be blown across the shrink film 150, where the air may be at a lower temperature than the heating area, or even cooler than ambient temperatures. In embodiments, the shrink film 150 may be cooled to a temperature at or below about 80° C., at or below about 70° C., at or below about 60° C., at or below about 50° C., at or below about 40° C., or even at or below about 30° C. Following processing in the cooling zone 224, the shrink wrap may undergo additional cooling on the conveyor 210 once the testing vehicle 100 has exited the shrink tunnel 220.

Generally, the shrink film 150 applies a force on the testing vehicle 100 during cooling. However, the shrink film 150 may apply a force on the testing vehicle 100 during the heating step as well as during the cooling step. As the shrink film 150 is shrunken, the forces applied by the shrink film 150 on the testing vehicle 100 are measured with the force sensors at the multiple separate sensor positions. The measurements may be taken during processing, after processing, or both, where "processing" refers to shrinking the shrink film 150. The measurements may be translated into force data, which can be analyzed. In one embodiment, different force sensors may measure the relatively low applied forces during heating and the relatively high applied forces during cooling. For example, as described above, force sensors with different measurement thresholds may be utilized. The applied forces may be recorded over the time period of the shrinking so that the forces during heating and forces during cooling may be separately analyzed. In one embodiment, the force data may be analyzed with a time sequenced video of the testing vehicle 100 that shows the shrink film 150 shrinking during processing.

Furthermore, it should be understood that while FIG. 6 depicts a shrink tunnel 220 embodiment, it should be understood that the shrink film processing unit 200 may be any system operable to shrink a shrink film 150. For example, the shrink film processing unit 200 may be a stationary heating and cooling process, where the testing vehicle 100 does not move during the shrinking.

The force data, or other collected data, may be analyzed to determine whether any material or process changes may improve the shrink film 150. For example, based on the data observed by the testing vehicle 150, a wide variety of process parameters and materials may be changed such as, but not limited to, resin compositions and layer structures that comprise the film, such as the properties and parameters related to the composition and structure, including the ratio of LDPE to LLDPE, autoclave versus tubular LDPE compositions, molecular weights and molecular weight distributions of the resins for film fabrication, and balanced versus unbalanced layer structures; film processing conditions, for example, the melt temperatures, blow up ratios, and/or draw down and cooling conditions; the shrink processing unit (e.g., shrink tunnel) conditions, for example, tunnel temperatures and profiles, air speed, air flow conditions, and/or residence time.

For the purposes of describing and defining the present invention it is noted that the terms "about" or "approximately" are utilized herein to represent the inherent degree of uncertainty that may be attributed to any quantitative comparison, value, measurement, or other representation. The term is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

It is also noted that recitations herein refer to a component of the present invention being "configured" in a particular way. In this respect, such a component is "configured" to embody a particular property, or function in a particular manner, where such recitations are structural recitations as opposed to recitations of intended use. More specifically, the references herein to the manner in which a component is "configured" denotes an existing physical condition of the component and, as such, is to be taken as a definite recitation of the structural characteristics of the component.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for measuring the forces of a shrink film, the method comprising:
    providing a shrink film processing unit and a testing vehicle moveable within the shrink film processing unit, wherein the testing vehicle comprises a three-dimensional frame structure comprising length, width, and height dimensions, and a plurality of force sensors positioned at multiple separate sensor positions proximate an outer surface of the three-dimensional frame structure, wherein the plurality of force sensors are arranged at multiple separate sensor positions in order to measure forces in the direction of the length, the width, and the height dimensions of the three-dimensional frame structure;
    positioning a shrink film around the testing vehicle, wherein the testing vehicle is at least partially wrapped by the shrink film in a non-shrunken state;
    processing the wrapped testing vehicle by shrinking the shrink film around the testing vehicle as the testing vehicle moves through the shrink film processing unit; and
    measuring the forces applied by the shrink film on the testing vehicle with the force sensors at the multiple separate sensor positions during processing, after processing, or both; and
    wherein one or more of:
        one or more of the force sensors comprises a pin member positioned in a channel of the frame structure;
        one or more of the force sensors is positioned within a depression of the frame structure; or
        force sensors are positioned on an outer face, an outer corner, and an outer edge of the outer surface of the three-dimensional frame structure.

2. The method of claim 1, wherein one or more of the force sensors comprises a pin member positioned in a channel of the frame structure.

3. The method of claim 1, wherein one or more of the force sensors is positioned within a depression of the frame structure.

4. The method of claim 1, wherein force sensors are positioned on an outer face, an outer corner, and an outer edge of the outer surface of the three-dimensional frame structure.

5. The method of claim 1, wherein the shrink film processing unit is a shrink tunnel.

6. The method of claim 1, wherein the shrink film comprises polyolefin material.

7. The method of claim 1, wherein the three-dimension frame structure is size-adjustable.

8. The method of claim 1, wherein processing the shrink film comprises heating the shrink film to a temperature of at least about 110° C., and following the heating, cooling the shrink film to a temperature at or below about 50° C.

9. The method of claim 1, further comprising a controller comprising a processor and memory, wherein the controller receives and stores force data from the force sensors.

10. The method of claim 1, wherein the testing vehicle further comprises one or more temperature-measuring devices.

11. A system for measuring the force of shrink film, the system comprising:
    a shrink film processing unit comprising a heating zone and a cooling zone downstream of the heating zone; and
    a testing vehicle moveable within the shrink film processing unit, wherein the testing vehicle comprises a three-dimensional frame structure comprising length, width, and height dimensions, and a plurality of force sensors positioned on multiple separate sensor positions proximate an outer surface of the three-dimensional frame structure, wherein the plurality of force sensors are arranged at multiple separate sensors positions in order to measure forces in the direction of the length, the width, and the height dimensions of the three-dimensional frame structure; and
    wherein one or more of:
        one or more of the force sensors comprises a pin member positioned in a channel of the frame structure;
        one or more of the force sensors is positioned within a depression of the frame structure; or
        force sensors are positioned on an outer face, an outer corner, and an outer edge of the outer surface of the three-dimensional frame structure.

12. The system of claim 11, wherein force sensors are positioned on an outer face, an outer corner, and an outer edge of the outer surface of the three-dimensional frame structure.

13. The system of claim 11, wherein the shrink film processing unit is a shrink tunnel.

14. The system of claim 11, wherein the three-dimensional frame structure comprises a generally rectangular prism shape.

15. The system of claim 11, wherein the heating zone is configured to operate at a temperature of at least about 110° C. and the cooling zone is configured to operate at a temperature at or below about room temperature.

16. The system of claim 11, further comprising a controller comprising a processor and memory, wherein the controller is configured to receive and store force data from the force sensors.

17. The system of claim 16, further comprising an automated film applicator positioned upstream of the shrink film processing unit.

18. The system of claim 11, wherein one or more of the force sensors comprises a pin member positioned in a channel of the frame structure.

19. The system of claim 11, wherein one or more of the force sensors is positioned within a depression of the frame structure.

* * * * *